(12) United States Patent
Ochs et al.

(10) Patent No.: US 6,317,635 B1
(45) Date of Patent: Nov. 13, 2001

(54) SENSOR RESPONSIVE ELECTROTHERAPY APPARATUS

(76) Inventors: Dennis E. Ochs, 2528 170th Pl. SE., Bellevue, WA (US) 98008; Daniel J. Powers, 2145 Squak Mountain Loop SW., Issaquah, WA (US) 98027

( * ) Notice: Subject to any disclaimer, the term of this patent is extended or adjusted under 35 U.S.C. 154(b) by 0 days.

(21) Appl. No.: 09/345,590

(22) Filed: Jun. 30, 1999

(51) Int. Cl.$^7$ ....................... A61N 1/08
(52) U.S. Cl. ............................. 607/62
(58) Field of Search ................ 607/5–8, 62, 63

(56) References Cited

U.S. PATENT DOCUMENTS

| | | |
|---|---|---|
| 3,747,605 | 7/1973 | Cook. |
| 3,860,009 * | 1/1975 | Bell et al. ............ 128/419 |
| 5,115,807 * | 5/1992 | Pless et al. ............ 128/419 |
| 5,350,403 * | 9/1994 | Stroetmann et al. ............ 607/5 |
| 5,593,427 | 1/1997 | Gliner et al. ............ 607/7 |
| 5,601,612 | 2/1997 | Gliner et al. ............ 607/7 |
| 5,607,454 | 3/1997 | Cameron et al. ............ 607/5 |
| 5,620,470 | 4/1997 | Gliner et al. ............ 607/7 |
| 5,836,978 | 11/1998 | Gliner et al. . |

FOREIGN PATENT DOCUMENTS

| | | |
|---|---|---|
| 2348139A | 9/2000 | (GB). |
| WO95/09673 | 4/1995 | (WO). |
| WO97/31680 | 9/1997 | (WO). |
| WO98/47563 | 10/1998 | (WO). |

* cited by examiner

Primary Examiner—William E. Kamm

(57) ABSTRACT

An electrotherapy apparatus includes a connecting mechanism coupled between an energy source and a pair of electrodes for contacting a patient. A controller coupled to the energy source configures the energy source to provide a selected one of a plurality of energy levels. The controller actuates the connecting mechanism to couple the energy source to the electrodes. A sensor coupled to the controller measures a parameter or parameters related to the energy delivered to the patient through the electrodes. The controller performs an operation using the output received from the sensor. Based upon the operation, the controller actuates the connecting mechanism to decouple the energy source from the electrodes. In an embodiment of the electrotherapy apparatus, the energy source includes a high voltage power supply for charging a capacitor to a selected one of a plurality of initial voltages. The sensor includes a voltage sensor to measure the voltage across the capacitor and a current sensor to measure the current supplied by the capacitor. The connecting mechanism includes electronic switches coupled between the capacitor and the electrodes to permit application of an electrotherapy waveform in either polarity. The controller performs the operation using the measured voltages and currents to control the electronic switches. The operation may include computing the patient impedance, determining a time constant of the voltage or current, determining a quantity of charge delivered to the patient, or determining the time required for the voltage or current to substantially equal a predetermined fraction of the voltage or current.

15 Claims, 2 Drawing Sheets

SENSOR RESPONSIVE ELECTROTHERAPY APPARATUS

FIELD OF THE INVENTION

This invention relates to the field of electrotherapy. More particularly, this invention relates to a hardware implementation of an electrotherapy apparatus and a method for using the electrotherapy apparatus.

BACKGROUND OF THE INVENTION

Some electrotherapy apparatuses used to perform electrotherapy dynamically control the electrotherapy waveform applied to the patient in response to real time impedance measurements made upon the patient. Hardware implementations of these electrotherapy apparatuses measure such parameters as the charge delivered to the patient or the voltage of the electrotherapy waveform applied to the patient to estimate the impedance. In response to these measurements, the electrotherapy apparatuses adjust the electrotherapy waveform delivered to the patient to improve the effectiveness of the electrotherapy.

Electrotherapy apparatuses that dynamically control the electrotherapy waveform applied to the patient have implemented threshold comparison functions in hardware. The hardware has included such things as comparators using voltage references to determine when a measured parameter has reached a threshold value. A cost savings and a reliability improvement could be realized if the hardware required for implementing the threshold comparison could be simplified. A need exists for an electrotherapy apparatus having reduced hardware complexity.

SUMMARY OF THE INVENTION

Accordingly, an implementation of an electrotherapy apparatus having reduced hardware and a method for using the electrotherapy apparatus have been developed. An electrotherapy apparatus for performing electrotherapy on a patient through a first electrode and a second electrode includes an energy source to provide energy for performing the electrotherapy and a connecting meckanism configured for coupling and decoupling the energy source, respectively, to and from the first electrode and the second electrode. The electrotherapy apparatus also includes a first sensor configured for measuring a first parameter related to the energy supplied to the patient by the energy source. Additionally, the electrotherapy apparatus includes a controller arranged to receive the first parameter from the first sensor. The controller is configured to perform an operation, using the first parameter, for actuating the connecting mechanism to decouple the energy source from the first electrode and from the second electrode.

An electrotherapy apparatus includes an energy source and a controller. A method for performing electrotherapy on a patient includes coupling the energy source to the patient. The method also includes measuring a first parameter related to energy supplied to the patient. Additionally, the method includes performing an operation upon the first parameter using the controller. The method further includes decoupling the energy source from the patient based upon the operation.

A defibrillator for delivering a multi-phasic waveform to a patient through a first electrode and a second electrode includes a capacitor having a first terminal and having a second terminal. The capacitor stores charge used for delivery of the multi-phasic waveform to the patient. The defibrillator further includes a first sensor configured for measuring a first parameter related to the energy supplied to the patient by the capacitor. Additionally, the defibrillator includes a connecting mechanism coupled between the first terminal and the second terminal of capacitor and the first electrode and the second electrode. The connecting mechanism permits the first terminal of the capacitor to selectively couple to one of the first electrode and the second electrode and to permit the second terminal of the capacitor to selectively couple to one of the first electrode and the second electrode. The defibrillator also includes a controller arranged to receive the first parameter from the sensor. The controller is configured to perform an operation, using the first parameter, for actuating the connecting mechanism to decouple the capacitor from the first electrode and the second electrode. The defibrillator also includes a power supply configured for charging the capacitor to an initial voltage determined by the controller.

DESCRIPTION OF THE DRAWINGS

A more thorough understanding of the invention may be had from the consideration of the following detailed description taken in conjunction with the accompanying drawings in which.

DETAILED DESCRIPTION OF THE DRAWINGS

Figure 1:
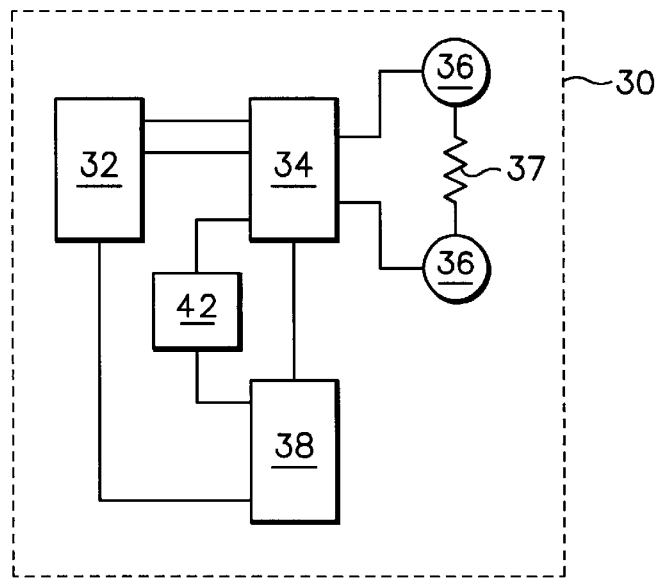
FIG. 1 shows a high level block diagram of an electrotherapy apparatus.

The present invention is not limited to the embodiments disclosed in this specification. Although the exemplary embodiments of the electrotherapy apparatus will be discussed in the context of an external defibrillator, the principles illustrated are applicable to an internal defibrillator. Additionally, although one of the exemplary embodiments of the electrotherapy apparatus is configured for delivering a bi-phasic electrotherapy waveform, the principles illustrated are applicable to an electrotherapy apparatus which delivers other electrotherapy waveforms such as a monophasic electrotherapy waveform, multi-phasic electrotherapy waveform, a damped sinusoid electrotherapy waveform, or the like.

Compensation for impedance variations between patients involves the measurement of one or more parameters related to the energy delivered to the patient. These parameters could include, for example, voltage or current supplied to the patient by the electrotherapy apparatus. The measured parameters, or the results of computations on the measured parameters, are compared to threshold values. Based upon the result of the comparison, the electrotherapy waveform is adjusted during its application to compensate for impedance variations between patients. Previously, comparison of the measured values of the parameters to the threshold values was done using dedicated hardware by using comparators. Additionally, the threshold values themselves have typically been set using dedicated hardware such as voltage references. The voltage references have been implemented in a variety of ways, such as by using voltage dividers, zener diodes, or integrated circuit voltage references.

A reduction in hardware complexity could be achieved by performing an operation on the parameters using programmable hardware. By using firmware or software to control the hardware with the threshold values specified in the code, the additional hardware complexity that would be required to implement the threshold comparison functions is eliminated. An additional advantage achieved under program control is the capability to easily configure the electrotherapy apparatus to deliver one of a plurality of energy levels. Under program control, the operation performed on the parameters is adjusted depending upon the selected energy level and the different threshold values that can be coded in the software, or firmware, are easily selected.

Yet another advantage of an implementation under program control is the improved reliability achieved by reducing the hardware required. A hardware implementation using a plurality of threshold values for delivering one of a plurality of possible energy levels to the patient would require additional hardware to establish a plurality of reference values and a plurality of comparators to perform the comparison. Alternatively, a switching mechanism could be used to selectively connect the plurality of reference values to a single comparator. This increased complexity decreases the reliability of the electrotherapy apparatus.

Shown in FIG. 1 is a high level block diagram of an electrotherapy apparatus 30, such as a defibrillator. The electrotherapy apparatus 30 performs electrotherapy on patients and compensates for impedance variations between patients by dynamically controlling the electrotherapy waveform applied to the patients. The implementation of electrotherapy apparatus 30 shown in FIG. 1 is a reduced hardware implementation. In the electrotherapy apparatus 30, functions previously implemented using dedicated hardware are accomplished by the operation performed in controller 38 under program control, thereby reducing the hardware complexity needed for electrotherapy apparatus 30.

Electrotherapy apparatus 30 includes an energy source 32 to provide the energy for the electrotherapy waveform. Energy source 32 may include, for example, a single capacitor or a capacitor bank arranged to act as a single capacitor. A connecting mechanism 34 selectively connects and disconnects energy source 32 to and from a pair of electrodes 36 contacting a patient, with the impedance of the patient represented here as a resistive load 37. Connecting mechanism 34 selectively connects energy source 32 to resistive load 37 to provide an electrotherapy waveform. Connecting mechanism 34 can selectively connect either side of energy source 32 to either one of electrodes 36 to provide an electrotherapy waveform of either polarity. Controller 38 actuates the connecting mechanism 34 to couple energy source 32 to electrodes 36 or to decouple energy source 32 from electrodes 36.

Electrotherapy apparatus 30 could be configured to provide a variety of electrotherapy waveforms to a patient, such as a mono-phasic electrotherapy waveform, a truncated exponential bi-phasic waveform, a damped sinusoidal waveform, or the like. Energy source 32, connecting mechanism 34, and controller 38 could be designed to selectively permit delivery of any of these types of electrotherapy waveforms to the patient. Additionally, the electrotherapy waveforms may be delivered by energy source 32 using a selected one of a plurality of energy levels set by controller 38.

Controller 38 is coupled to sensor 42 and receives the output it generates. Sensor 42 measures a parameter, or parameters, related to the energy delivered to the patient. Sensor 42 may be, for example, a voltage sensor, a current sensor, or sensor 42 could be configured to measure both voltage and current. Controller 39 uses the values of the parameter or parameters provided by sensor 42 to control connecting mechanism 34. The operation performed by controller 38 could include comparing threshold values to the output received from sensor 42. Based upon the result of this comparison, controller 38 actuates connecting mechanism 34 to control the duration of the electrotherapy waveform applied to resistive load 37. Connecting mechanism 34 can be actuated to either couple energy source 32 to patient electrodes 36 or decouple energy source 32 from patient electrodes 36 based upon the operation. The operation could include directly determining the duration of the electrotherapy waveform based upon the results of the comparison. Alternatively, the operation performed by controller 38 on the values of the parameter or parameters received from sensor 42 may include integrating a current measured by sensor 42 to determine the charge delivered to the patient. Or, it could include determining patient impedance, computing a time constant, or determining the time required for a current or voltage to substantially equal a predetermined fraction of the initial voltage or current. In this alternative, the operation would also include comparing the results of these computations to threshold values accessed by controller 38.

Using controller 38, operating under program control, to perform the operation using the values output from sensor 42 and threshold values simplifies the hardware needed to implement electrotherapy apparatus 30. For example, in previous implementations of electrotherapy apparatuses, integrations were performed in hardware using analog integrators. The result of the integration was compared to a threshold value using dedicated hardware. By using controller 38 to perform the integration and comparison to the threshold value under program control, the dedicated hardware is eliminated. An additional benefit from performing integration under program control is the ability to achieve a greater dynamic range in the integration more easily than using dedicated hardware. This allows for dynamic control of the electrotherapy waveform using threshold values (that may, for example, be specified in terms of the charge delivered to the patient) that can be more simply implemented over a broader range of values with greater accuracy than for a dedicated hardware integrator. Similarly, determining patient impedance, time constants, or the time required for voltages or currents to substantially equal predetermined threshold values, is more easily done over a wide range of energy levels by performing the operation using controller 38 than by using dedicated hardware.

In electrotherapy apparatus 30, threshold values for other parameters, such as the maximum allowable current supplied Vindicating the possibility of a short circuit) or the minimum current supplied by the electrotherapy apparatus 30 (indicating a possible open circuit) may be implemented in the software or firmware operating controller 38. Performing these comparisons under program control allows a reduction in the hardware needed to perform the over current and under current detection functions. Previously, dedicated hardware in addition to that needed for dynamic waveform control) was used to accomplish the over current and under current detection.

Figure 2:
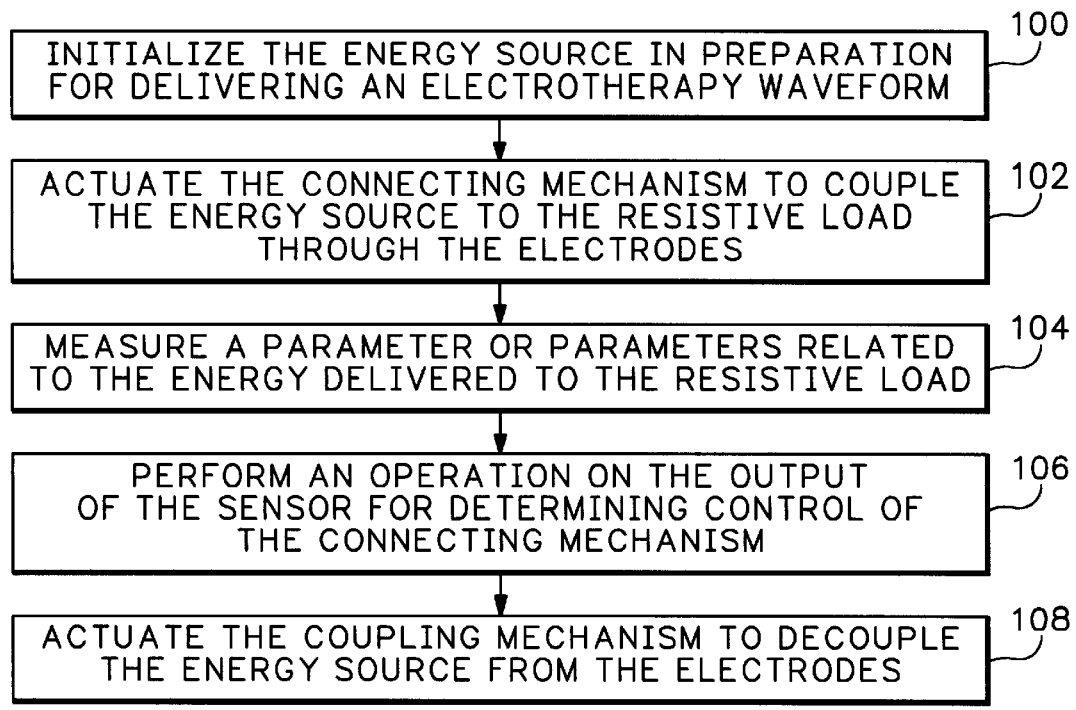
FIG. 2 shows a high level flow diagram of a method for using the electrotherapy apparatus shown in FIG. 1 to apply electrotherapy to a patient.

Shown in FIG. 2 is a high level flow diagram of a method for using the hardware shown in FIG. 1 to perform electrotherapy. First, in step 100, controller 38 initializes energy source 32 in preparation for delivering an electrotherapy waveform to resistive load 37. Next, in step 102, controller 38 actuates connecting mechanism 34 to couple energy source 32 to resistive load 37 through electrodes 36. Then, in step 104, sensor 42 measures a parameter, or parameters, related to the energy delivered to resistive load 37. Next, in step 106, controller 38 performs an operation on the output received from sensor 42 for determining control of connecting mechanism 34. The operation may include determining the charge delivered to the patient, determining a patient impedance, determining a time constant, or determining the time required for a current or voltage to substantially equal a predetermined fraction of the initial voltage or current. Then, in step 108, controller 38 actuates connecting mechanism 34 to decouple energy source 32 from electrodes 36 to control the electrotherapy waveform applied to resistive load 37 (representative of the patient impedance) based upon the parameter. The decoupling is done based upon the operation to compensate for impedance variations between patients.

Figure 3:
FIG. 3 shows an exemplary electrotherapy waveform that could be applied to a patient using the electrotherapy apparatus shown in FIG. 1.

Shown in FIG. 3 is an exemplary electrotherapy waveform that could be applied to a patient using electrotherapy apparatus 30. Although the exemplary electrotherapy waveform shown in FIG. 3 is a bi-phasic waveform, it should be recognized that electrotherapy apparatus 30 could be configured to deliver a mono-phasic waveform or an electrotherapy waveform having more than two phases.

Figure 4:
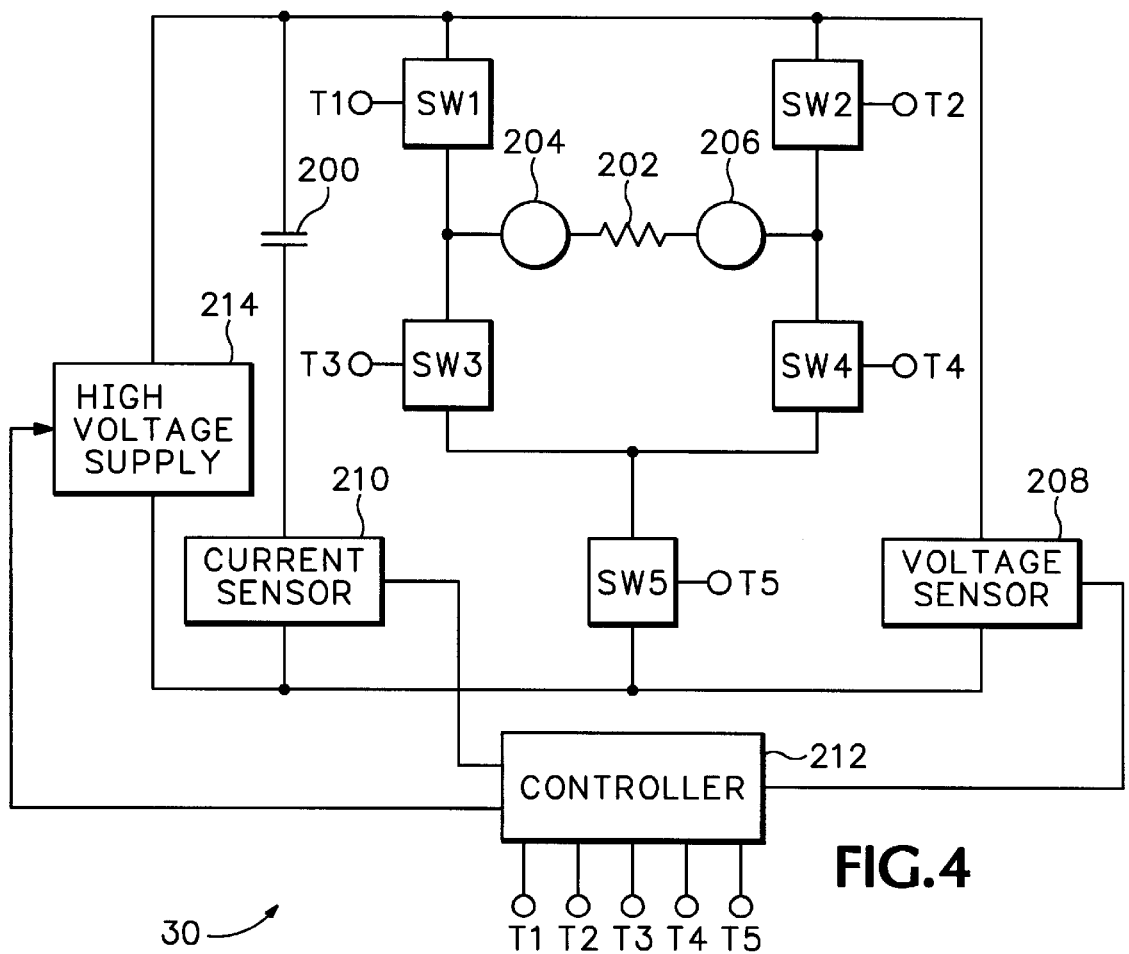
FIG. 4 shows a simplified schematic of an embodiment of the electrotherapy apparatus shown in FIG. 1.

Shown in FIG. 4 is a simplified block diagram showing an embodiment of electrotherapy apparatus 30 that performs the operation under firmware control. The embodiment of electrotherapy apparatus 30 shown in FIG. 4 can be configured for delivering a multi-phasic electrotherapy waveform to the patient, such as the bi-phasic waveform shown in FIG. 3. Although FIG. 4 shows a specific electrotherapy apparatus that performs the operation, the disclosed principles are broadly applicable to electrotherapy apparatuses.

A limitation of a dedicated hardware implementation using multiple threshold values for delivery of multiple energy levels to the patient is the complexity of the dedicated hardware required. The implementation of this capability would require dedicated hardware to set the multiple threshold values and dedicated hardware to selectively compare the output from the sensors to the threshold values. However, in the embodiment of the electrotherapy apparatus 30 shown in FIG. 4, these functions are easily implemented in the firmware that operates controller 212.

The embodiment of the electrotherapy apparatus 30 shown in FIG. 4 includes sensors to measure the voltage and current supplied by capacitor 200 to patient impedance 202 through first electrode 204 and second electrode 206. Measurement of the voltage supplied by capacitor 200 is performed by voltage sensor 208. Voltage sensor 208 could, for example, be implemented using a voltage divider network and a buffer amplifier coupled to the voltage divider. The voltage divider generates a scaled version of the voltage on capacitor 200 for the buffer amplifier. The voltage from the voltage divider is coupled to the buffer amplifier. Measurement of the current supplied by capacitor 200 is performed by current sensor 210. Current sensor 210 could, for example, be implemented using a sense resistor coupled in series with capacitor 200 and an amplifier coupled across the sense resistor. The sense resistor generates a voltage proportional to the current flowing from capacitor 200. The voltage output from the amplifier is a scaled version of the voltage across the sense resistor. Voltage sensor 208 and current sensor 210 are each coupled to controller 212. Controller 212 measures the output from each of these sensors. Controller 212 can use the values of the parameters measured by voltage sensor 208 and current sensor 210 to dynamically control the electrotherapy waveform supplied to the patient. Dynamic control could be based upon the current supplied to the patient, the charge supplied to the patient, the voltage supplied to the patient, or a combination of these.

Controller 212 performs the operation on the values of the parameters received from one or both of voltage sensor 208 and current sensor 210. Based upon the operation, switches SW1, SW2, SW3, SW4, and SW5 are closed and opened to deliver a multi-phasic electrotherapy waveform to patient impedance 202 through first electrode 204 and second electrode 206. The duration of each of the phases of the multi-phasic waveform are determined by the operation performed by controller 212 on the values of the parameters received from one or both of voltage sensor 208 and current sensor 210. By controlling the duration of the phases, the embodiment of the electrotherapy apparatus 30 can deliver differently shaped electrotherapy waveforms to the patient. The operation performed by controller 212 that determines the durations of each of the phases could be accomplished by computations using the values of the measured parameters. Alternatively, the operation performed by controller 212 that determines the durations of each of the phases could be accomplished with values in a lookup table accessed by controller 212 using the values of the measured parameters.

The operation performed by controller 212 on the values of the parameters measured by voltage sensor 208 and current sensor 210 depends upon the method chosen to implement the dynamic electrotherapy waveform control. For example, controller 212 could measure either the voltage or current supplied over a period of time after the application of the electrotherapy waveform to compute a time constant. The time constant is dependent upon the value of capacitor 200 and the resistance in series with this capacitance. The series resistance includes the patient impedance and the resistance in the discharge path of the capacitor. Control of the electrotherapy waveform based upon the time constant value would involve sampling either the voltage or current supplied by capacitor 200, computing the time constant of the electrotherapy waveform from these values, and then dynamically controlling the waveform using the computed time constant value. One way to determine the time constant value would involve computing the slope of the logarithm of the voltage versus time curve for the electrotherapy waveform applied to the patient. Using the time constant value, the durations of the phases of the electrotherapy waveform would be selected from a lookup table or computed by controller 212. For a bi-phasic electrotherapy waveform, the information in the lookup table would have first phase durations corresponding to ranges of time constant values. The duration of the second phase could also be specified in the lookup table or computed based upon the duration of the first phase.

Alternatively, the operation performed by controller 212 could dynamically control the electrotherapy waveform applied to the patient based upon a time interval required for the voltage or current supplied to the patient to substantially equal a predetermined fraction of a value of voltage or current measured during application of the electrotherapy waveform. This value of voltage or current could be the peak value of the voltage or current measured near the beginning of the electrotherapy waveform. Or, this value of voltage or current could be measured at other times during the application of the electrotherapy waveform. For example, this value of voltage or current could be measured after the instant at which the peak current or voltage occurs.

For dynamic waveform control based upon measurements by voltage sensor 208, controller 212 could read the voltage measured by voltage sensor 208 (the voltage across capacitor 200 which closely approximates the voltage applied to patient impedance 2021 at the time capacitor 200 is coupled to patient impedance 202. This corresponds to the peak value of the voltage supplied to the patient during application of the electrotherapy waveform. Alternatively, because controller 212 is used in selecting the initial voltage to which capacitor 200 is charged, controller 212 could use the value of the selected initial voltage of capacitor 200 as the peak voltage supplied by capacitor 200. In another alternative, the voltage on capacitor 200 after the occurrence of the peak voltage could be measured and used by controller 212 to perform the operation. The operation performed by controller 212 would include computing a threshold value as a predetermined fraction of the value of the voltage on capacitor 200 (either measured or selected). The time interval required for the voltage across capacitor 200 to substantially equal the threshold value changes depending upon the magnitude of patient impedance 202. The time interval will be shorter for low impedance patients than it is for high impedance patients. Based upon this time interval, the operation performed with controller 212 would also include computing, or selecting from a lookup table, the durations of the phases of the multi-phasic electrotherapy waveform, such as the first phase or the second phase of a bi-phasic waveform.

Dynamic control of the electrotherapy waveform could also be accomplished by determining a time interval required for the current supplied by capacitor 200 to substantially equal a predetermined fraction of the peak value of the current supplied by capacitor 200. To accomplish this, the controller 212 would read the measurement of the current supplied by capacitor 200 made by current sensor 210 to determine the peak current supplied to patient impedance 202. Typically, when electrotherapy is applied, the current supplied to patient impedance 202 will rise from zero to a peak value shortly after capacitor 200 is coupled to the patient. The rise time from zero to the peak value is limited by the inductance in the path through which the current flows. After reaching the peak value, the current will decay toward zero at a rate determined primarily by the value of capacitor 200 and the series resistance (which includes patient impedance 202). The operation performed by controller 212 would include computing a threshold value as a predetermined fraction of the peak value of the current. As an alternative to measuring the peak current to compute a threshold value, controller 212 could read the measurement of the current supplied by capacitor 200 after the occurrence of the peak current. The threshold value would be computed as a predetermined fraction of this measured current.

The time interval required for the current supplied to patient impedance 202 to substantially equal the threshold value of the current changes depending upon the magnitude of patient impedance 202. The time interval will be shorter for low impedance patients than it is for high impedance patients. The operation performed by the controller 212 would further include determining the time interval required for the current supplied by capacitor 200 to substantially equal the threshold value. Based upon this time interval, the operation performed by controller 212 would also include computing, or selecting from a lookup table, the durations of the phases of the multi-phasic electrotherapy waveform, such as the first phase and the second phase of a bi-phasic electrotherapy waveform.

In yet another dynamic electrotherapy waveform control technique, the operation performed by controller 212 would involve determining the value of patient impedance 202. Controller 212 would read the voltage and current values from, respectively, voltage sensor 208 and current sensor 210. The operation performed by controller 212 would include computing the value of patient impedance 202 based upon the voltage and current values. Computation of patient impedance 202 by controller 212 could be done using a single voltage value and a single current value measured substantially simultaneously, or, alternatively, a plurality of pairs of voltage values and current values measured substantially simultaneously at various times after the start of the electrotherapy waveform.

The plurality of pairs of voltage values and current values would be used by the controller to calculate multiple instantaneous values of the patient impedance during application of the electrotherapy waveform. The operation performed by controller 212 could include averaging these values of patient impedance. Averaging of the impedance values provides a more accurate measurement of the patient impedance than would be obtained from single measurements of voltage and current. The measurements and computation of the patient impedances would be done relatively early in the application of the electrotherapy waveform so that the results could be used to adjust the electrotherapy waveform based upon the calculated patient impedance. Based upon the computed impedance value, the operation performed by controller 212 would also include computing, or selecting from a lookup table, the durations of the phases of the multi-phasic electrotherapy waveform, such as the first phase and the second phase of a bi-phasic electrotherapy waveform.

An additional technique for dynamic control of the electrotherapy waveform determines the duration of the phases of a multi-phasic electrotherapy waveform depending based upon the charge delivered to the patient. Controller 212 reads the values of current measured by current sensor 210 after application of the electrotherapy waveform to the patient. The operation performed by controller 212 includes integrating these current values to determine the charge delivered to the patient over the time in which the measurements were made. The operation performed by controller 212 further includes determining a time interval required for delivering a predetermined quantity of charge to the patient. Based upon the time interval, the operation performed by controller 212 would also include computing, or selecting from a lookup table, the durations of the phases of the multi-phasic electrotherapy waveform, such as the first phase and the second phase of a bi-phasic electrotherapy waveform.

An energy source, such as high voltage power supply 214, is used to charge capacitor 200 to an initial voltage determined by controller 212. The initial voltage to which capacitor 200 is charged sets the energy level of the electrotherapy waveform to be applied to patient impedance 202. The initial voltage is selected by controller 212 from one of a plurality of possible initial voltages values. Selecting from a plurality of initial voltages values for charging capacitor 200 is done in response to operator input. An operator may need to select the initial voltage because electrotherapy will be applied to the heart, or to a pediatric patient.

Controller 212 dynamically controls the electrotherapy waveform applied to patient impedance 202 based upon the parameters supplied by the sensors. Dynamic control of the electrotherapy waveform permits patients having a wide range of impedances to receive optimal levels of energy. Depending upon the technique used to perform the dynamic waveform control, the operation performed by controller 212 may need to account for the initial voltage to which capacitor 200 is charged to deliver optimal levels of energy to patients having varying impedances. The threshold values used in the operation performed by controller 212 may change depending upon the initial voltage to which capacitor 200 is charged. In performing the operation, controller 212 would use a threshold value corresponding to the selected one of the plurality of initial voltage values. For dynamic electrotherapy waveform control based upon the operation, the threshold values used by controller 212 would be computed or selected from a lookup table dependent upon the energy level applied to the patient. For each of the plurality of initial voltages to which capacitor 200 could be charged, there would be a corresponding threshold value used in the operation performed by controller 212. Using a plurality of threshold values is easily done because the different threshold values are selected by the firmware of controller 212.

In addition to dynamic electrotherapy waveform control, the embodiment of electrotherapy apparatus 30 shown in FIG. 4 is also well suited to the detection of over-current and under-current conditions during the application of electrotherapy. Current sensor 210 measures the current supplied by capacitor 200 at the end of the first 100 micro-seconds following application of the electrotherapy waveform to detect the over-current or under-current condition. The threshold values that indicate the presence of either an over-current condition or an under-current condition change with the energy level used for the electrotherapy.

Detection of either an over-current or an under-current condition results in termination of the electrotherapy waveform. The presence of an under-current condition indicates the possibility of damaged electrodes or electrodes that are not connected to the patient. The presence of an over-current condition indicates the possibility of a short circuit. The threshold values for the over-current and the under-current detection can be computed from the initial voltage to which capacitor 200 is charged. The initial voltage could be obtained by reading the output of voltage sensor 208. Alternatively, the threshold values for the over-current and the under-current detection can be selected from a lookup table based upon the initial voltage to which capacitor 200 is charged. The threshold values are computed by controller 212 using the upper and lower limits of the expected values of patient impedance 202 (respectively, 180 ohms and 25 ohms) and subtracting or adding a small value to provide for possible measurement error. The values of the measured current road from current sensor 210 are compared by controller 212 to the corresponding threshold values to determine whether an over-current or an under-current condition is present.

Operation of the embodiment of electrotherapy apparatus 30 shown in FIG. 4 will be explained for the case in which switch SW5 is an insulated gate bipolar transistor and switches SW1–SW4 are silicon controlled rectifiers. However, it should be recognized that other types of electronic or electro-mechanical switches could be used to deliver the electrotherapy waveform. For other types of switching devices, the order in which switches SW1–SW5 are actuated may be different. Additionally, operation of the embodiment of electrotherapy apparatus 30 will be explained for the case in which the multi-phasic waveform applied includes a bi-phasic waveform.

In preparation for delivering a bi-phasic electrotherapy waveform, controller 212 configures high voltage power supply 214 to charge capacitor 200 to a selected initial voltage. Then controller 212 closes switch SW5 to prepare for delivering the first phase of a bi-phasic waveform. Next, switches SW1 and SW4 are closed to begin the first phase of the bi-phasic electrotherapy waveform. After the beginning of the first phase, voltage sensor 208 measures the voltage across capacitor 200 and current sensor 210 measures the current supplied by capacitor 200. Based upon the values of either the voltage or the current or the values of both the voltage and the current, controller 212 performs an operation to determine the duration of the first phase and the second phase. At the end of the time interval determined for the first phase, controller 212 opens switch SW5. This interrupts current flow through switches SW1 and SW4 and opens these switches, completing the first phase. After 400 micro-seconds, controller 212 closes switch SW5 to prepare for delivering the second phase of the bi-phasic waveform. Then, 50 micro-seconds later, switches SW2 and SW3 are closed to begin the second phase. At the end of the time interval determined for the second phase, controller 212 opens switch SW5. This interrupts current flow through switches SW2 and SW3 and opens these switches completing the second phase.

Although several embodiments of the invention have been disclosed, various modifications may be made without departing from the scope of the appended claims.

What is claimed is:

1. An electrotherapy apparatus for performing electrotherapy on a patient through a first electrode and a second electrode, the electrotherapy apparatus comprising:
   an energy source to provide energy for performing the electrotherapy;
   a connecting mechanism configured for coupling and decoupling the energy source, respectively, to and from the first electrode and the second electrode;
   a first sensor configured for measuring a first parameter related to the energy supplied to the patient by the energy source; and
   a controller arranged to receive the first parameter from the first sensor and configured to perform an operation , using the first parameter, for actuating the connecting mechanism to decouple the energy source from the first electrode and the second electrode, wherein:
   the operation includes determining a time constant based upon the first parameter.

2. The electrotherapy apparatus as recited in claim 1, wherein:
   the controller includes a configuration to control the energy source to provide a selected one of a plurality of energy levels for the electrotherapy and to perform the operation using a value corresponding to the selected one of the plurality of energy levels for the electrotherapy.

3. The electrotherapy apparatus as recited in claim 2, wherein:
   the controller includes a configuration to actuate the connecting mechanism to perform a first phase of the electrotherapy having a first duration based upon the operation and to actuate the connecting mechanism to perform a second phase of the electrotherapy having a second duration based upon the operation.

4. The electrotherapy apparatus as recited in claim 3, wherein:
   the first parameter includes either a current or a voltage supplied by the energy source to the patient.

5. An electrotherapy apparatus for performing electrotherapy on a patient through a first electrode and a second electrode, the electrotherapy apparatus comprising:
   an energy source to provide energy for performing the electrotherapy;

a connecting mechanism configured for coupling and decoupling the energy source, respectively, to and from the first electrode and the second electrode;

a first sensor configured for measuring a first parameter related to the energy supplied to the patient by the energy source; and a controller arranged to receive the first parameter from the first sensor and configured to perform an operation, using the first parameter, for actuating the connecting mechanism to decouple the energy source from the first electrode and the second electrode, wherein:

the operation includes determining a first time interval beginning with the first sensor measuring a first value of the first parameter and ending with the first sensor measuring a second value of the first parameter substantially equal to a predetermined fraction of the first value; and the controller includes a configuration to actuate the connecting mechanism to couple the energy source to the first electrode and the second electrode and to decouple the energy source from the first electrode and the second electrode at the end of a second time interval determined by the operation and having a first duration based upon the first time interval.

6. The electrotherapy apparatus as recited in claim 5, wherein:

the controller includes a configuration to actuate the connecting mechanism to couple the energy source to the first electrode and the second electrode after the second time interval and to decouple the energy source from the first electrode and the second electrode at the end of a third time interval determined by the operation and having a second duration based upon the first time interval.

7. The electrotherapy apparatus as recited in claim 6, wherein:

the controller includes a configuration to control the energy source to provide a selected one of a plurality of energy levels for the electrotherapy and to perform the operation to determine the second time interval and the third time interval using a value corresponding to the selected one of the plurality of energy levels for the electrotherapy.

8. The electrotherapy apparatus as recited in claim 7, wherein:

the first parameter includes either a current or a voltage supplied by the energy source to the patient.

9. An electrotherapy apparatus for performing electrotherapy on a patient through a first electrode and a second electrode, the electrotherapy apparatus comprising:

an energy source to provide energy for performing the electrotherapy;

a connecting mechanism configured for coupling and decoupling the energy source, respectively, to and from the first electrode and the second electrode;

a first sensor configured for measuring a first parameter related to the energy supplied to the patient by the energy source; and a controller arranged to receive the first parameter from the first sensor and configured to perform an operation, using the first parameter, for actuating the connecting mechanism to decouple the energy source from the first electrode and the second electrode, wherein:

the first parameter includes a current supplied by the energy source to the patient;

the operation includes determining a charge delivered to the patient using the first parameter and determining a first time interval beginning with the coupling of the energy source to the first electrode and the second electrode and ending with the charge delivered to the patient substantially equaling a predetermined value; and the controller includes a configuration to actuate the connecting mechanism to couple the energy source to the first electrode and the second electrode and to decouple the energy source from the first electrode and the second electrode at the end of a second time interval determined by the operation and having a first duration based upon the first time interval.

10. The electrotherapy apparatus as recited in claim 9, wherein:

the controller includes a configuration to actuate the connecting mechanism to couple the energy source to the first electrode and the second electrode after the second time interval and to decouple the energy source from the first electrode and the second electrode at the end of a third time interval determined by the operation and having a second duration based upon the first time interval.

11. The electrotherapy apparatus as recited in claim 10, wherein:

the controller includes a configuration to control the energy source to provide a selected one of a plurality of energy levels for the electrotherapy and to perform the operation to determine the second time interval and the third time interval using a value corresponding to the selected one of the plurality of energy levels for the electrotherapy.

12. The electrotherapy apparatus as recited in claim 11, wherein:

the energy source includes a capacitor coupled to a power supply; and the energy source includes a configuration to charge the capacitor to a selected one of a plurality of voltages corresponding to the selected one of the plurality of energy levels.

13. The electrotherapy apparatus as recited in claim 12, wherein:

the operation includes determining the first time interval based upon a time required for the charge delivered to the patient to substantially equal a selected one of a plurality of predetermined values, including the predetermined value, corresponding to the selected one of the plurality of voltages.

14. The electrotherapy apparatus as recited in claim 13, wherein:

the controller includes a configuration to determine a maximum allowable current and a minimum allowable current based upon the selected one of the plurality of voltages and to actuate the connecting mechanism to decouple the energy source from the first electrode and the second electrode for a value of the first parameter greater than the maximum allowable current or less than the minimum allowable current.

15. An electrotherapy apparatus for performing electrotherapy on a patient through a first electrode and a second electrode, the electrotherapy apparatus comprising:

an energy source to provide energy for performing the electrotherapy;

a connecting mechanism configured for coupling and decoupling the energy source, respectively, to and from the first electrode and the second electrode;

a first sensor configured for measuring a first parameter related to the energy supplied to the patient by the energy source;

a memory storing a threshold value and a set of program instructions; and a processing unit coupled to the memory and the first sensor, the processing unit configured to perform a comparison operation in accordance with the set of program instructions, using the first parameter and the threshold value stored in the memory, for actuating the connecting mechanism to decouple the energy source from the first electrode and the second electrode.

* * * * *